US00PP33064P2

(12) United States Plant Patent
de Gruyter

(10) Patent No.: US PP33,064 P2
(45) Date of Patent: May 11, 2021

(54) ***SALVIA* PLANT NAMED 'GRUSALVUL'**

(50) Latin Name: ***Salvia* hybrid**
Varietal Denomination: GRUSALVUL

(71) Applicant: André de Gruyter B.V., Rockanje (NL)

(72) Inventor: Andre de Gruyter, Rockanje (NL)

(73) Assignee: André de Gruyter B.V., Rockanje (NL)

( * ) Notice: Subject to any disclaimer, the term of this patent is extended or adjusted under 35 U.S.C. 154(b) by 0 days.

(21) Appl. No.: 16/873,490

(22) Filed: Apr. 21, 2020

(51) Int. Cl.
*A01H 6/50* (2018.01)
*A01H 5/02* (2018.01)

(52) U.S. Cl.
USPC ..... Plt./475

(58) Field of Classification Search
USPC ..... Plt./475
See application file for complete search history.

(56) References Cited

PUBLICATIONS

Pluto Plant Variety Database for Application 20170671, Sep. 15, 2020.*
Pluto Plant Variety Database for Application 20180241, Sep. 15, 2020.*

* cited by examiner

*Primary Examiner* — Annette H Para
(74) *Attorney, Agent, or Firm* — Samuel R. McCoy, Jr.

(57) ABSTRACT

'GRUSALVUL' is a new and distinctive *Salvia* plant which is characterized by a broad upright growth habit, a broad inverted triangular plant form, an abundance of pink flowers borne on long inflorescences that sit above the foliage, and plants bearing a large number of inflorescences at once. The new variety propagates successfully by stem cuttings and has shown to be uniform and stable in the resulting generations from asexual propagation.

3 Drawing Sheets

Latin name of the genus and species: The Latin name of the genus and species of the novel variety disclosed herein is *Salvia* hybrid.

Variety denomination: The inventive variety of *Salvia* disclosed herein has been given the variety denomination 'GRUSALVUL'.

BACKGROUND OF THE INVENTION

Parentage: 'GRUSALVUL' is a hybrid seedling selection resulting from the controlled pollination of *Salvia* x *sylvestris* 'Rianne' (Community Plant Variety Rights grant number 41746), the seed parent, with *Salvia nemorosa* 'Pink Friesland' (U.S. Plant Pat. No. 18,152), the pollen parent, at a commercial nursery in Rockanje, the Netherlands in July of 2017. The crossing was made by the inventor in July of 2017 at a commercial greenhouse in Rockanje, the Netherlands. In September of 2017, one seedling was observed which exhibited unique growth and foliage characteristics. The seedling was isolated for further evaluation in order to confirm the distinctness and stability of the characteristics first observed. Upon confirmation of distinctness and stability, 'GRUSALVUL' was selected for commercialization.

Asexual Reproduction: Asexual reproduction of 'GRUSALVUL' was first accomplished in September of 2017 by rooting softwood stem cuttings at a commercial greenhouse in Rockanje, the Netherlands. Five successive generations have shown that the unique features of the instant cultivar are stable and reproduce true to type.

SUMMARY OF THE INVENTION

The cultivar 'GRUSALVUL' has not been observed under all possible environmental conditions and the phenotype may vary somewhat with variations in the instant environment such as temperature, day length, and light intensity, without, however, any variance in genotype. The following traits have been repeatedly observed and represent the distinguishing characteristics of the new *Salvia* plant, 'GRUSALVUL'.

1. *Salvia* 'GRUSALVUL' exhibits a broad, upright growth habit with a broad, inverted triangular plant profile; and
2. *Salvia* 'GRUSALVUL' exhibits an abundance of pink labiate flowers borne on long terminal verticillaster inflorescences that sit above the foliage; and
3. *Salvia* 'GRUSALVUL' exhibits a floriferous flowering habit with plants bearing a large number of inflorescences at once.

BOTANICAL DESCRIPTION OF THE PLANT

Figure 1:
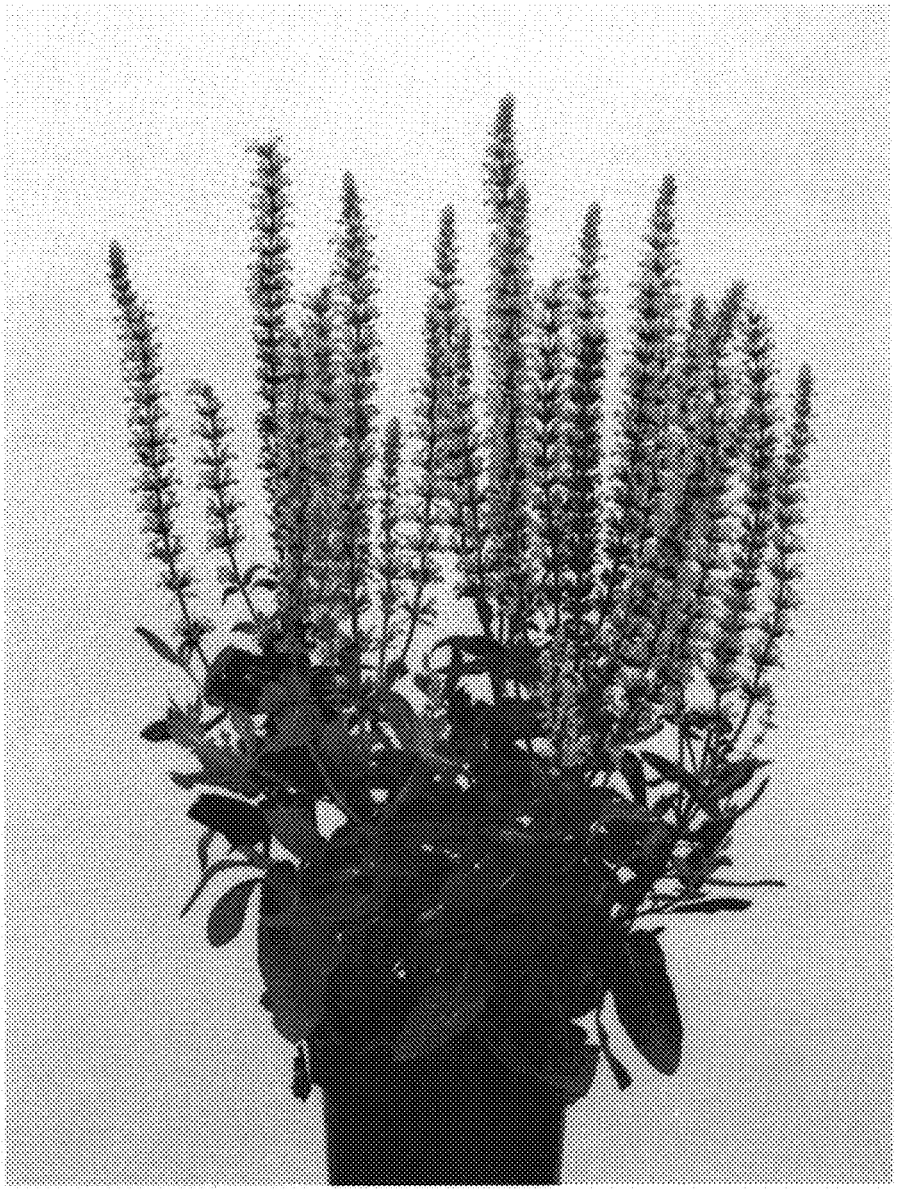
FIG. 1 shows, as nearly true as it is reasonably possible to make the same in color illustrations of this type, an exemplary 'GRUSALVUL' plant at approximately 3 months old, potted into an 11 cm nursery pot, grown in a greenhouse in Rockajne, the Netherlands.
Figure 2:
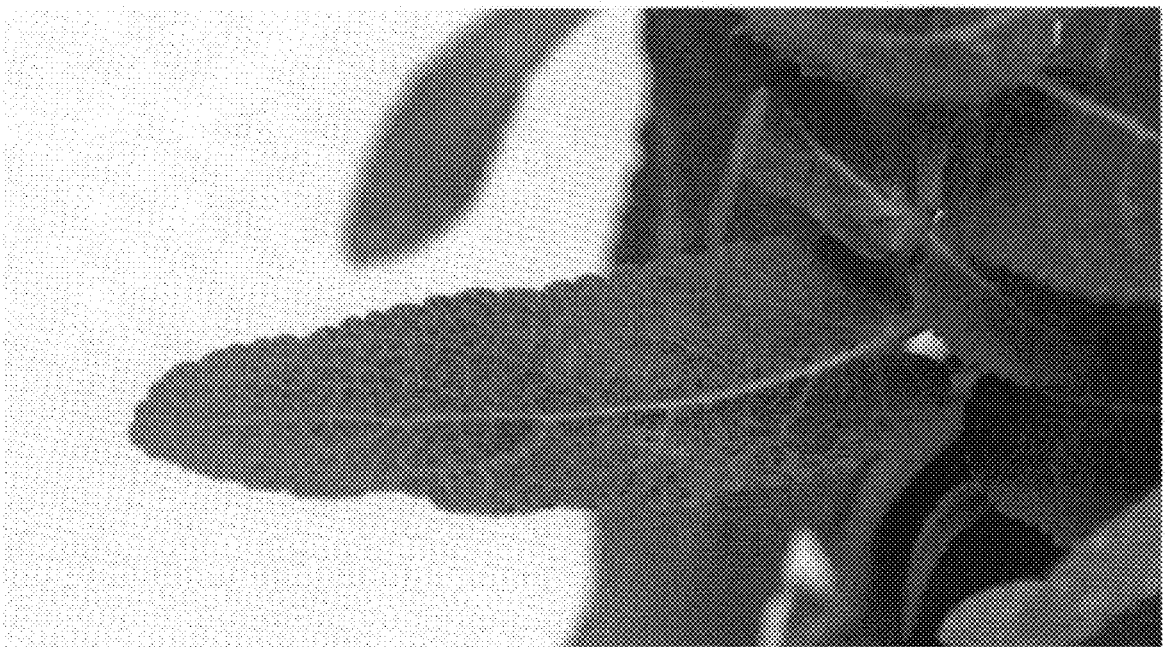
FIG. 2 shows, as nearly true as it is reasonably possible to make the same in color illustrations of this type, the typical foliage of 'GRUSALVUL'.
Figure 3:
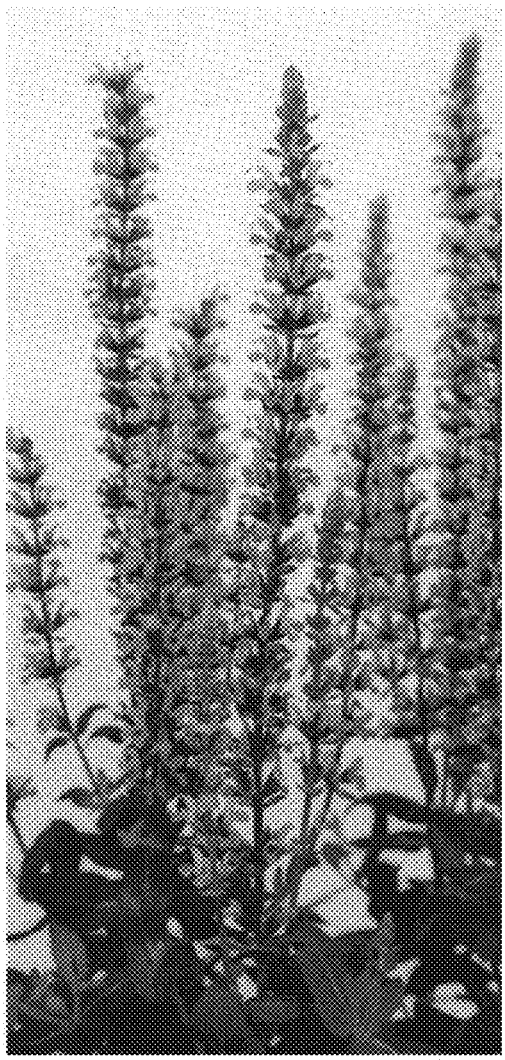
FIG. 3 shows, as nearly true as it is reasonably possible to make the same in color illustrations of this type, the typical inflorescence of 'GRUSALVUL'.

The following is a detailed botanical description of a new and distinct variety of *Salvia* known as 'GRUSALVUL', based upon observations of 3 month old plants in 11 cm nursery containers, grown outdoors in Rockanje, the Netherlands. Plants were grown using conventional field production protocols for *Salvia* plants which consisted of regular overhead irrigation. No pest or disease control measures were utilized in production. Temperatures ranged between 18 to 35 degrees Celsius during the day and 12 to 22 degrees Celsius at night. Plants were produced with full sun exposure and no photoperiodic treatments or artificial light was given to the plants. Observation data was recorded in September of 2019.

Those skilled in the art will appreciate that certain characteristics will vary with older or, conversely, with younger plants. 'GRUSALVUL' has not been observed under all possible environmental conditions. Where dimensions, sizes, colors and other characteristics are given, it is to be understood that such measurements are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 2015 edition.

A botanical description of 'GRUSALVUL' and comparisons with the parent plants and most similar variety of common knowledge are provided below.

General plant description:

*Growth habit*.—A broad, upright herbaceous perennial.

*Plant profile*.—Broad, inverted triangular.

*Height*.—19.0 cm to the top of the foliar plane; 36.9 cm to the top of the floral plane.

*Spread*.—32.2 cm.

*Plant vigor*.—Moderate vigorous.

*Growth rate*.—Moderately fast growing.

*Propagation*.—Softwood stem cuttings; rooting is initiated in approximately 10 days when grown in a greenhouse with an ambient average temperature of 18 degrees Celsius.

*Time to produce a finished plant*.—Approximately 12 weeks are required to produce a marketable finished plant in a 13 cm pot.

*Pest resistance and susceptibility*.—Not any more or less tolerant or susceptible to pests or diseases known to effect *Salvia*.

*Environmental tolerances*.—Adapt to, at least, USDA Zones 3 to 10 and temperatures ranging from minus 28 degrees Celsius to 40 degrees Celsius; moderate to high tolerance to rain; moderate tolerance to wind.

Root system: Thin, fibrous, and freely branched.

Stem:

*Branching habit*.—Basally branching main stems growing from a caudex; freely branching with short lateral branches. Stems and branches emit a slight fragrance when touched, typical for the species. Pinching isn't required but will improve branching.

*Number of main stems per plant*.—6.

*Number of lateral branches per plant*.—24.

*Main stem length*.—15.0 cm, excluding the inflorescence.

*Main stem diameter*.—3.0 cm.

*Internode length*.—2.7 cm.

*Texture*.—Moderately pubescent; very short, soft hairs with an average length of 0.08 cm and colored translucent white, RHS N155A.

*Luster*.—Matte.

*Aspect*.—Main stems are upright; lateral branches are at an average angle of 55 degrees to the main stems (varying between 20 and 90 degrees).

*Strength*.—Strong.

*Color, juvenile*.—Yellow-green, nearest RHS 145B.

*Color, mature*.—Yellow-green, nearest to in between RHS 146B and 146C, and moderately blotched with greyed-purple, nearest to RHS N186C.

*Color at internodes*.—Yellow-green, nearest to in between RHS 146B and 146C.

Foliage:

*Arrangement*.—Opposite.

*Attachment*.—Petiolate.

*Division*.—Simple.

*Abundance of foliage*.—Abundant.

*Lamina*.—Dimensions — 6.2 cm long and 3.2 cm wide, on average. Shape — Narrow ovate to oblong. Aspect — Flat to involute and slightly reflexed. Apex — Broad, bluntly acute. Base — Cordate. Margin — Crenate; not undulated. Pubescence and luster of adaxial surface — Smooth, glabrous, and very slightly glossy. Pubescence and luster of abaxial surface — Smooth, glabrous, and matte. Color — Juvenile foliage, adaxial surface — Yellow-green, nearest to RHS 144A. Juvenile foliage, abaxial surface — Yellow-green, nearest to RHS 144B. Mature foliage, adaxial surface — Green, nearest to RHS NN137A. Mature foliage, abaxial surface — Yellow-green, nearest to RHS 147B. Venation — Pattern — Pinnate. Venation color, adaxial surface — Yellow-green, nearest to in between 144B and 144C. Venation color, abaxial surface — Yellow-green, RHS 144C, becoming greyed-purple as leaves age, in between RHS 186A and 186B.

*Petiole*.—Length — 1.1 cm. Width — Petioles are flattened; 0.25 cm, horizontally, and 0.15 cm, vertically. Texture, adaxial surface — Glabrous. Texture, abaxial surface — Glabrous. Margins — Moderately pubescent with short hairs with an average length of 0.01 cm and colored greyed-white, nearest to RHS 156D. Luster, adaxial surface — Slightly glossy. Luster, abaxial surface — Slightly glossy. Color, adaxial surface — Yellow-green, nearest to RHS 145A. Color, abaxial surface — Yellow-green, nearest to RHS 145A. Strength — Strong.

Inflorescence:

*Type*.—Terminal verticillaster with individual flowers in whorls.

*Natural flowering season*.—Late spring into summer in Rockanje, the Netherlands.

*Time to flower*.—Approximately 10 weeks after flowering.

*Flowering habit*.—Freely flowering.

*Dimensions*.—An average of 21.2 cm high, not including peduncle, and 2.2 cm in diameter.

*Quantity of inflorescence per plant*.—20, on average.

*Quantity of flowers per inflorescence*.—Approximately 200 flowers and buds.

*Attitude*.—Upright.

*Peduncles*.—Length — 20.7 cm. Diameter — 0.15 cm. Aspect — Quadrangulate. Attitude — Upright; near vertical. Strength — Strong. Texture — Moderately pubescent; short glandular hairs with an average length of 0.05 cm and colored translucent white, nearest to RHS N155A. Luster — Matte. Color —

Green, RHS 143C, and very slightly blotched greyed-purple, RHS N186C.

Flower buds:

*Shape*.—Obovate.

*Length*.—Average of 0.55 cm.

*Diameter*.—0.175 cm, horizontally; 0.25 cm, vertically.

*Texture*.—Moderately pubescent; very short glandular hairs with an average length of 0.02 cm and colored white, nearest to RHS NN155D.

*Luster*.—Matte.

*Color*.—Greyed-green, RHS 197A, and fading to yellow-green towards the base, RHS 144B; veined purple, RHS N77C. Immature sepals are red-purple, RHS 71B, and finely dotted white, RHS NN155D.

Flower:

*Flowering habit*.—Freely flowering.

*Shape*.—Labiate.

*Dimensions of the flower height*.—Length is 1.0 cm, vertical height is 0.7 cm, and the horizontal width is 0.4 cm.

*Floral throat diameter*.—0.1 cm.

*Dimensions of the floral tube*.—Tube flattened; length is 0.45 cm, vertical height is 0.2 cm, and the horizontal width is 0.1 cm.

*Attitude*.—Outward facing.

*Fragrance*.—Non-fragrant.

*Lastingness*.—Approximately 10 days.

*Persistent*.—Self-cleaning.

*Pedicels*.—Dimensions — 0.2 cm long and 0.5 cm in diameter. Attitude — Upward; approximately 60 degrees to the peduncle axis. Strength — Moderately strong. Texture — Densely pubescent; short glandular hairs with an average length of 0.02 cm and colored translucent white, nearest to RHS NN155D. Luster — Matte. Color — Yellow-green, nearest to RHS N144A.

*Petals*.—Quantity of Petals — 2. Arrangement — Labiate; one upper lip and one lower lip which are fused at the proximal half of the petals. Shape of petal lobes — Upper lip is folded into an oblanceolate shape; lower lip is spatulate with a larger central lobe and two smaller lateral lobes. Dimensions, free portion of the upper petal — 0.55 cm long and 0.1 cm wide. Dimensions, free portion of the lower petal — 0.5 cm long and 0.4 cm wide. Apex — Upper lip is emarginate; lobes of the lower lip are obtuse. Base — Truncate; fused at the base. Margin — Both petal lobes with entire margins; upper petal not undulated and lower petal slightly undulated. Aspect, upper lip — Concave. Aspect, lower lip — Central lobe is carinate; lateral lobes are concave. Pubescence, texture and luster of upper surface — Both petals are glabrous, slightly velvety and matte. Pubescence, texture and luster of lower surface — Moderately pubescent with short glandular hairs that have an average length of 0.02 cm and are colored the same as the petal; slightly velvety and matte. Petal color when opening, upper surface — Upper petal — Purple, nearest to RHS 75B. Lower petal — Purple, nearest to RHS N78D. Petal color when opening, lower surface — Upper petal — Purple, nearest to RHS 75B, and finely dotted white, RHS NN155D. Lower petal — Purple, nearest to RHS 77C. Petal color when fully opened, upper surface — Upper petal — Purple, nearest to RHS 75A; no visible venation. Lower petal — Purple, nearest to RHS 77B; no visible venation. Petal color when fully opened, lower surface — Upper petal — Purple, nearest to RHS 75B, and finely dotted white, RHS NN155D; no visible venation. Lower petal — Purple, nearest to in between RHS 77B and 77C; no visible venation. Upper petal, faded color — Upper petal — Purple, RHS 77D. Lower petal — Central lobe is purple, RHS N75D; lateral lobes are purple, RHS 77D. Lower petal, faded color — Upper petal — Purple, RHS 77D. Lower petal — Central lobe is purple, RHS N75D; lateral lobes are purple, RHS 77D. Floral throat color — Purple, RHS NN78C; no visible venation. Floral tube color when fully opened, inner and outer surfaces — Purple, RHS 75D, and fading to white towards the base, nearest to RHS N155A; no visible venation.

*Calyx*.—Shape — Campanulate. Dimensions — Calyx is flattened; length is 0.55 cm, the height is 0.3 cm, and the width is 0.225 cm. Sepals — Length — 0.55 cm. Width — 0.225 cm. Arrangement — Campanulate; the proximal 60 percent of the sepals are fused. Quantity — 2. Shape — Both sepals are narrow oblanceolate. Apex — Upper sepal is emarginate to praemorse with three acute tips; lower sepal is cleft. Base — Fused. Sepal lobe margin — Both sepals are entire; not undulated; moderately pubescent with very short glandular hairs with an average length of 0.2 cm and colored white, nearest to RHS NN155D. Pubescence, texture and luster, upper surface — Both sepals are smooth, glabrous, and matte. Pubescence, texture and luster, lower surface — Both sepals are moderately pubescent with very short glandular hairs with an average length of 0.2 cm and colored white, nearest to RHS NN155D; matte. Color when opening, upper surface — Green, RHS 138A; veined darker green, RHS 139B. Color when opening, lower surface — Greyed-green, RHS 197A, and fading to yellow-green towards the base, RHS 144B; veined purple, RHS N77C. Color when fully opened, upper surface — Green, RHS 138A; veined darker green, RHS 139B. Color when fully opened, lower surface — Yellow-green, RHS 147A; veined purple, RHS N77A. Floral bract — Position — Below each floral bud. Quantity — 1. Shape — Broad ovate. Length — 0.7 cm. Width — 0.6 cm. Apex — Broad acute. Base — Broad cuneate. Margin — Entire. Pubescence, texture and luster, upper surface — Smooth, glabrous, and matte. Pubescence, texture and luster, lower surface — Smooth, glabrous, and matte. Color when fully opened, upper surface — Yellow-green, RHS 145B, and slightly suffused with greyed-purple, RNS 186D; veined green, RHS 137C. Color when fully opened, lower surface — Yellow-green, RHS 145B, and slightly suffused with greyed-purple, RNS 186D; veined green, RHS 137C.

Reproductive organs:

*Stamens*.—Quantity — 2. Anthers — Attachment — Basifixed. Shape — Narrow oblong. Dimensions — Approximately 0.1 cm long and 0.04 cm wide. Color — Yellow-white, nearest to RHS 158A. Filaments — Length — 0.15 cm, on average. Color — Purple, RHS 76B. Pollen, amount — Sparse. Pollen color — Greyed-yellow, nearest to RHS 160B.

*Pistil*.—Quantity — 1. Length — 1.2 cm. Style — Length — 1.1 cm. Color — Purple, RHS N80B, and fading to white towards the base, nearest to RHS NN155D. Stigma — Shape — Cleft; decurrent. Length — 0.1 cm. Diameter — 0.1 cm. Color — Purple, RHS N80A. Ovary Color — Yellow-green, RHS 144A.

Seed and fruit: No fruit or seeds have been detected to date.

COMPARISONS WITH THE PARENT PLANTS AND MOST SIMILAR VARIETY OF COMMON KNOWLEDGE

Plants of the new cultivar 'GRUSALVUL' differ from its seed parent, *Salvia* x *sylvestris* 'Rianne' (Community Plant Variety Rights grant number 41746), by the characteristics described in Table 1.

TABLE 1

| Characteristic | 'GRUSALVUL' | 'Rianne' |
|---|---|---|
| Peduncle length. | Longer than 'Rianne'. | Shorter than 'GRUSALVUL'. |
| General coloration of the flower at anthesis. | Light purple, appearing as pink. | Darker purple, appearing as violet. |

Plants of the new cultivar 'GRUSALVUL' differ from its pollen parent, *Salvia nemorosa* 'Pink Friesland' (U.S. Plant Pat. No. 18,152), by the characteristics described in Table 2.

TABLE 2

| Characteristic | 'GRUSALVUL' | 'Pink Friesland' |
|---|---|---|
| Inflorescence size. | Longer than 'Pink Friesland'. | Shorter than 'GRUSALVUL'. |
| Abundance of flowers. | More abundant than 'Pink Friesland'. | Less abundant than 'GRUSALVUL' |
| General coloration of the flower at anthesis. | Light purple, appearing as pink. | Red-purple, appearing as dark pink. |

Plants of the new cultivar 'GRUSALVUL' may be distinguished from its most similar known commercial comparator, *Salvia* 'Pink Dawn' (U.S. Plant Pat. No. 26,343), by the characteristics described in Table 3.

TABLE 3

| Characteristic | 'GRUSALVUL' | 'Pink Dawn' |
|---|---|---|
| Plant size. | Smaller than 'Pink Dawn'. | Larger than 'GRUSALVUL'. |
| Foliage size. | Smaller than 'Pink Dawn'. | Larger than 'GRUSALVUL'. |
| General coloration of the flower. | Darker pink. | Lighter pink. |

That which is claimed is:

1. A new and distinct variety of *Salvia* hybrid plant named 'GRUSALVUL', substantially as described and illustrated herein.

* * * * *